US00PP35597P3

(12) United States Plant Patent
Degenhardt

(10) Patent No.: US PP35,597 P3
(45) Date of Patent: Jan. 23, 2024

(54) ***TRIPSACUM DACTYLOIDES* X *MISCANTHUS SACCHARIFLORUS* PLANT NAMED 'MAMMOTH'**

(50) Latin Name: ***Tripsacum dactyloides* x *Miscanthus sacchariflorus***
Varietal Denomination: Mammoth

(71) Applicant: Dick Degenhardt, Boskoop (NL)

(72) Inventor: Dick Degenhardt, Boskoop (NL)

(73) Assignee: DUTCH PLANT FORCE BV, Zoetermeer (NL)

( * ) Notice: Subject to any disclaimer, the term of this patent is extended or adjusted under 35 U.S.C. 154(b) by 0 days.

(21) Appl. No.: 17/725,004

(22) Filed: Apr. 20, 2022

(65) Prior Publication Data

US 2023/0270033 P1 Aug. 24, 2023

(30) Foreign Application Priority Data

Jan. 18, 2022 (QZ) ..... PBR 20220164

(51) Int. Cl.
*A01H 5/12* (2018.01)
*A01H 6/46* (2018.01)

(52) U.S. Cl.
USPC ..... Plt./384

(58) Field of Classification Search
USPC ..... Plt./384
See application file for complete search history.

*Primary Examiner* — Karen M Redden
(74) *Attorney, Agent, or Firm* — Penny J. Aguirre

(57) ABSTRACT

A new cultivar of *Tripsacum dactyloides* x *Miscanthus sacchariflorus* plant named 'Mammoth' that is characterized by its highly vigorous growth habit, its very tall plant height, its strong upright stems that do not fall over or flop, its leaves that are green in color with white center veins, and its lack of flower production.

3 Drawing Sheets

Botanical classification: *Tripsacum dactyloides* x *Miscanthus sacchariflorus*.

Cultivar designation: 'Mammoth'.

CROSS-REFERENCE TO A RELATED APPLICATION

This application claims priority to European Community Plant Variety Office (CPVO) Plant Breeder's Rights Application No. 2022/0164 filed on Jan. 18, 2022 under 35 U.S.C. 119(f), the entire contents of which is incorporated by reference herein.

BACKGROUND OF THE INVENTION

The present invention relates to a new and distinct cultivar of *Tripsacum dactyloides* x *Miscanthus sacchariflorus* and will be referred to hereafter by its cultivar name, 'Mammoth'. 'Mammoth' represents a new cultivar of ornamental grass grown for landscape use.

The new cultivar resulted from a controlled breeding program conducted by the Inventor in Boskoop, The Netherlands. The goal of the breeding program was to develop a new ornamental grass with a vigorous growth habit and strong and tall that does not lodge (fall over). The Inventor made a cross in autumn of 2008 between unnamed and unpatented proprietary plants of *Tripsacum dactyloides* (female parent) and *Miscanthus sacchariflorus* (male parent) from the Inventor's breeding program. 'Mammoth' was selected as a single unique plant in summer 2010 from the resulting seedlings of the above cross.

Asexual propagation of the new cultivar was first accomplished by root cuttings by the Inventor in Boskoop, The Netherlands in autumn of 2010. Asexual propagation by root cuttings has determined that the characteristics of the new cultivar are stable and are reproduced true to type in successive generations.

SUMMARY OF THE INVENTION

The following traits have been repeatedly observed and are determined to be the characteristics of the new cultivar. These attributes in combination distinguish 'Mammoth' as a unique cultivar of ornamental grass.

1. 'Mammoth' exhibits a highly vigorous growth habit.
2. 'Mammoth' exhibits a very tall plant height.
3. 'Mammoth' exhibits strong upright stems that do not fall over or flop.
4. 'Mammoth' exhibits leaves that are green in color with white center veins.
5. 'Mammoth' exhibits no production of flowers.

The female parent of 'Mammoth' differs from 'Mammoth' in producing flowers and having a less vigorous plant habit, a shorter plant height, a more mounded plant shape, stems that are less upright that tend to flop and leaves that do not have a white center vein. The male parent of 'Mammoth' differs from 'Mammoth' in producing flowers and in having a much less vigorous plant habit, a much shorter plant height, leaves that are more narrow, and produces flowers. 'Mammoth' can be most closely compared to the cultivars *Miscanthus* x *giganteus* 'Aksel Olsen' (not patented) and *Miscanthus sacchariflorus* 'Robustus' (not patented). 'Aksel Olsen' is similar to 'Mammoth' in foliage color. 'Robustus' is similar to 'Mammoth' in plant shape and foliage color. 'Aksel Olsen' and 'Robustus' both differ from 'Mammoth' in having less vigorous growth habits, shorter plant heights, and in producing flowers.

BRIEF DESCRIPTION OF THE DRAWINGS

The accompanying color photographs illustrate the overall appearance and distinct characteristics of the new ornamental grass. The photographs were taken in November of plants 5 years in age as field grown in Boskoop, The Netherlands.

The photograph in FIG. 1. was taken of a row of 'Mammoth' plants and provides a view of the overall plant habit and general appearance of 'Mammoth'.

Figure 1:
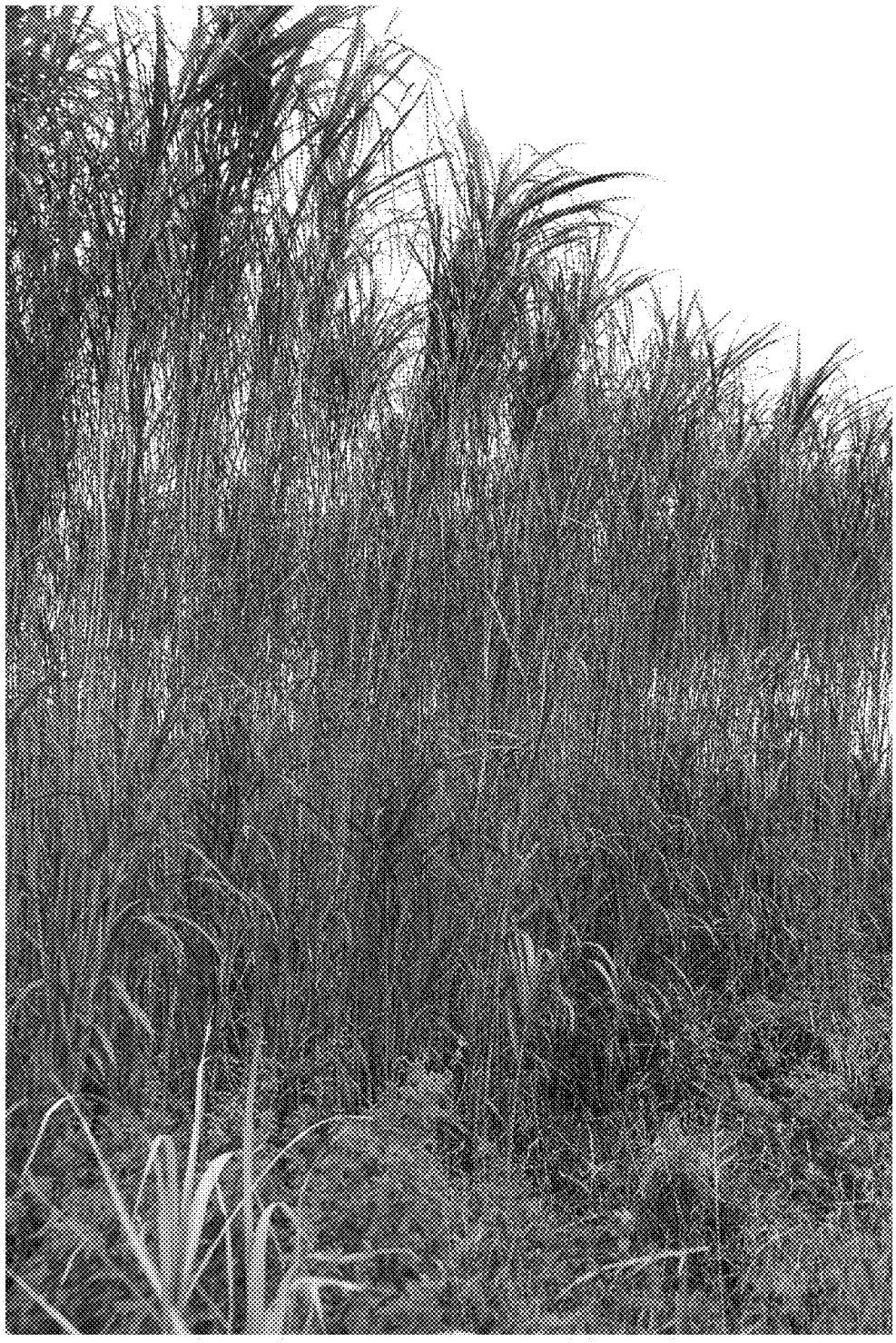
Figure 2:
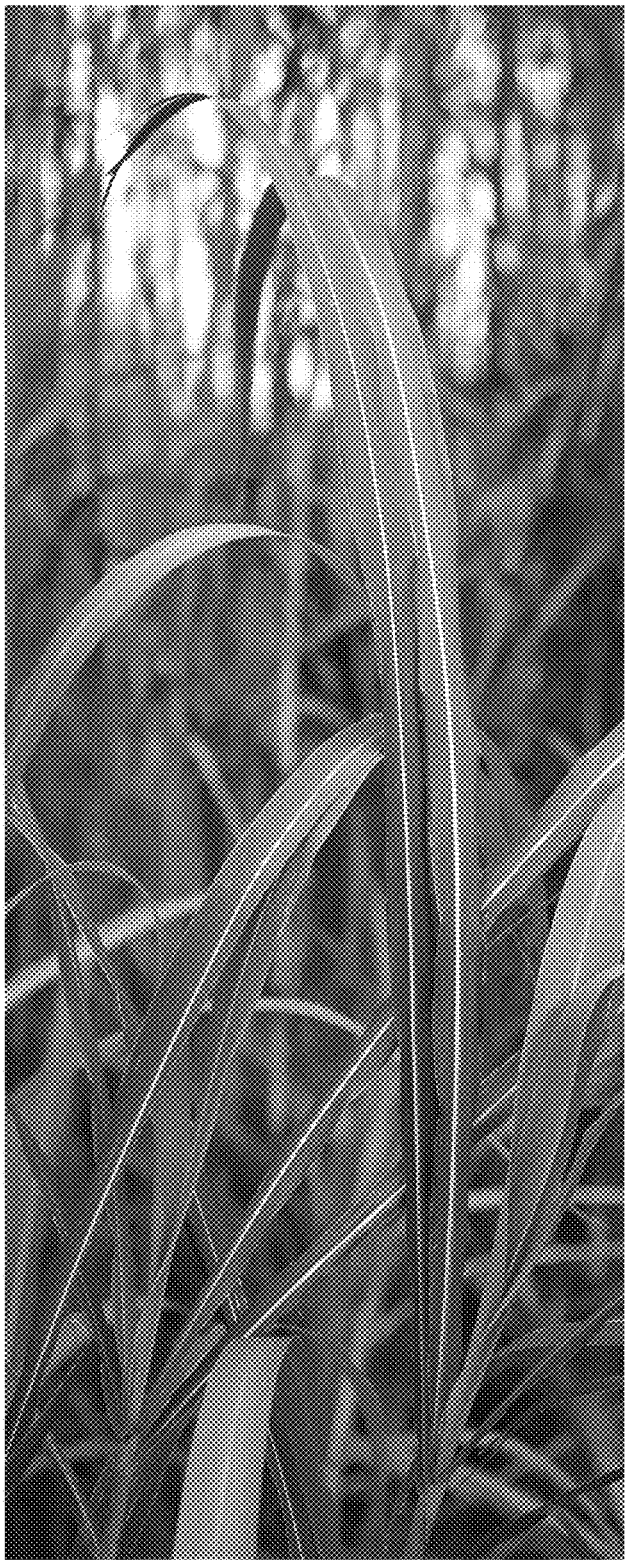

The photograph in FIG. 2. provides a close-up view of the foliage of 'Mammoth'.

Figure 3:
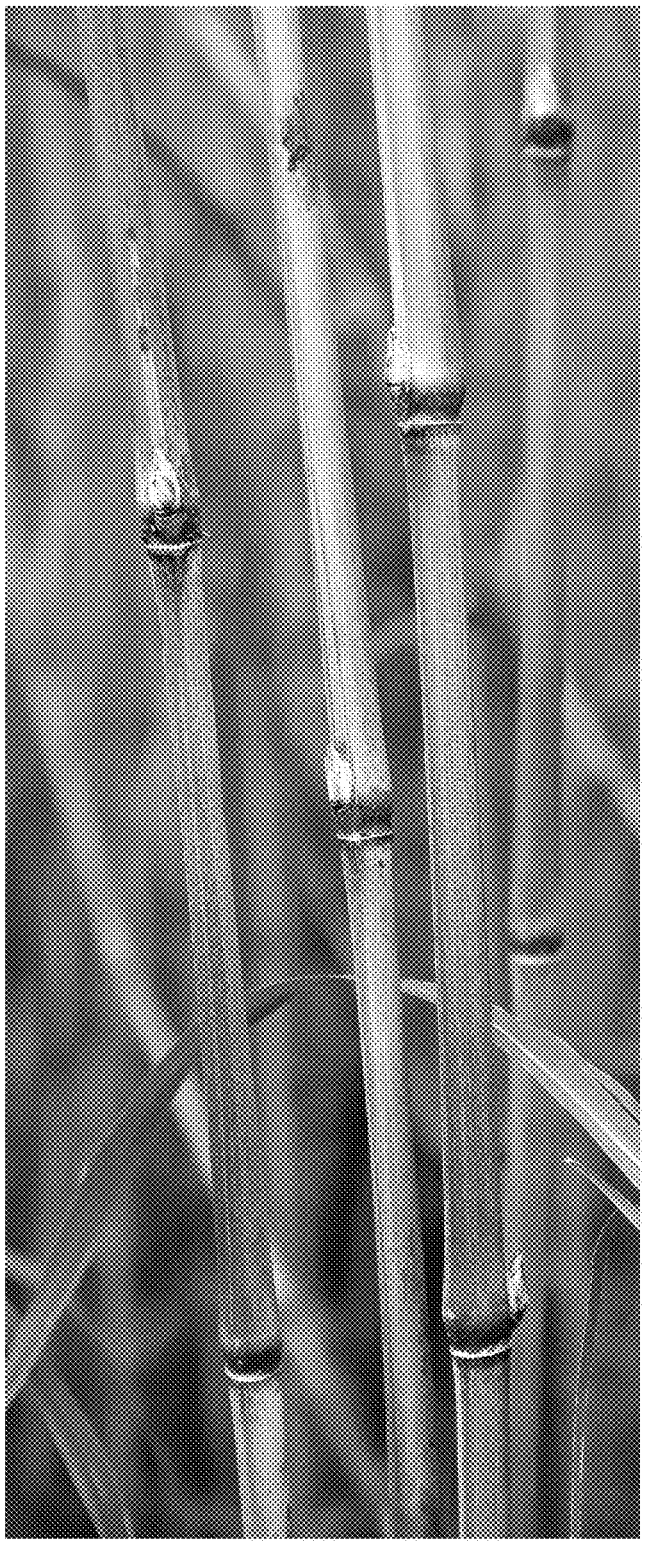

The photograph in FIG. 3. provides a close-up view of the stems of 'Mammoth'.

The colors in the photographs are as close as possible with the photographic and printing technology utilized and the color values cited in the Detailed Botanical Description accurately describe the colors of the new ornamental grass.

DETAILED BOTANICAL DESCRIPTION

The following is a detailed description of 5-year-old plants of the new cultivar as field grown in Boskoop, The Netherlands. The phenotype of the new cultivar may vary with variations in environmental, climatic, and cultural conditions, as it has not been tested under all possible environmental conditions. The color determination is in accordance with The 2015 Colour Chart of The Royal Horticultural Society, London, England, except where general color terms of ordinary dictionary significance are used.

General description:

*Plant type*.—Herbaceous perennial grass.

*Plant habit*.—Very upright with stems that do not lodge.

*Height and spread*.—Average of 53 m in height and 22 m in spread as a 5-year-old plant in the landscape.

*Cold hardiness*.—At least in U.S.D.A. Zone 6.

*Diseases and pests*.—No susceptibility or resistance to diseases or pests has been observed.

*Root description*.—Fibrous.

*Root development*.—An average of 6 months to produce a young rooted plant from a root cutting.

*Propagation*.—Root cuttings.

*Growth rate*.—Highly vigorous.

Stem description:

*General*.—Rounded, strong.

*Stem aspect*.—Growing from the base, held upright, vertically.

*Stem quantity*.—Average of 12 basal shoots and 1 lateral per basal shoot.

*Stem color*.—Young; 145C, mature; 148B, matte down 195A to 195D, internodes 146A and 146B, tinged 153D and 167D, older stems 153D, tinged 167D.

*Stem size*.—An average of 46 m in length (from base of shoots to base of inflorescence), 1.9 cm in diameter.

*Stem surface*.—Both surfaces moderately glossy and covered with a matte down.

Foliage description:

*Leaf shape*.—Linear.

*Leaf division*.—Simple.

*Leaf base*.—Sheathed.

*Leaf apex*.—Narrow and long acuminate.

*Leaf aspect*.—Slightly carinate, moderately arching.

*Leaf venation*.—Parallel, main vein furrowed, upper surface color 155C, lower surface color N144A.

*Leaf margins*.—Entire, visibly smooth, when rubbed downwards becoming very sharp.

*Internode length*.—An average of 21.9 cm.

*Leaf size*.—An average of 83.3 cm in length, an average of 3.2 cm in width, sheath; 21.9 cm in length, 2.2 cm in width (folded open).

*Leaf surface*.—Upper and lower surface glabrous and smooth, non-rugose, ligules; moderately pubescent with thin hairs an average of 1.5 mm in length and 156D in color.

*Leaf number*.—An average of 14 per shoot.

*Leaf arrangement*.—Alternate.

*Leaf color*.—Young upper surface; 144A, young lower surface 143A and 144A, mature upper and lower surface NN137C, sheath; inner side 194B, outer side 146B.

Flower description: No flowers have been produced to date.

It is claimed:

1. A new and distinct cultivar of *Tripsacum dactyloides* x *Miscanthus sacchariflorus* plant named 'Mammoth' as herein illustrated and described.

* * * * *